(12) United States Patent
Evans et al.

(10) Patent No.: US 10,266,741 B2
(45) Date of Patent: Apr. 23, 2019

(54) APPARATUS AND METHOD FOR ADDITION OF ADH ENZYME INHIBITORS TO EXISTING ENGINE COOLING SYSTEMS

(71) Applicants: John W. Evans, Sharon, CT (US); Steven J. Pressley, Sharon, CT (US)

(72) Inventors: John W. Evans, Sharon, CT (US); Steven J. Pressley, Sharon, CT (US)

( * ) Notice: Subject to any disclaimer, the term of this patent is extended or adjusted under 35 U.S.C. 154(b) by 0 days.

(21) Appl. No.: 15/596,336

(22) Filed: May 16, 2017

(65) Prior Publication Data

US 2017/0327721 A1 Nov. 16, 2017

Related U.S. Application Data

(60) Provisional application No. 62/391,997, filed on May 16, 2016.

(51) Int. Cl.
*C09K 5/20* (2006.01)
*C12N 9/04* (2006.01)

(52) U.S. Cl.
CPC .............. *C09K 5/20* (2013.01); *C12N 9/0006* (2013.01); *C12Y 101/01001* (2013.01)

(58) Field of Classification Search
CPC .......... C09K 5/20; C09K 5/10; C12N 9/0006; C12Y 101/01001
See application file for complete search history.

(56) References Cited

U.S. PATENT DOCUMENTS

| | | | |
|---|---|---|---|
| 3,108,075 A * | 10/1963 | Hearst | C09K 3/185 252/70 |
| 8,137,579 B2 | 3/2012 | Evans | |
| 8,206,607 B2 * | 6/2012 | Evans | C09K 5/20 252/67 |
| 8,394,287 B2 | 3/2013 | Evans et al. | |
| 8,431,038 B2 | 4/2013 | Evans et al. | |
| 2002/0171063 A1 * | 11/2002 | Evans | C09K 5/10 252/71 |
| 2003/0071242 A1 * | 4/2003 | Evans | C09K 5/10 252/73 |
| 2009/0057607 A1 * | 3/2009 | Evans | C09K 5/10 252/73 |
| 2014/0264150 A1 * | 9/2014 | Domingo | C09K 5/20 252/73 |

* cited by examiner

*Primary Examiner* — Long T Tran
(74) *Attorney, Agent, or Firm* — Grossman, Tucker, Perreault & Pfleger, PLLC

(57) ABSTRACT

An apparatus and method for the addition of alcohol dehydrogenase (ADH) enzyme inhibitors to existing engine cooling systems to reduce or eliminate the coolant toxicity without the need to completely drain and replace the entire engine coolant. In addition, the present invention provides an apparatus and method for treatment of otherwise toxic coolants removed from engine cooling systems that are targeted for disposal and release into the environment and thereby reduce or eliminate the condition of creating relatively large amounts of toxic waste during routine maintenance and repairs.

11 Claims, 2 Drawing Sheets

ND METHOD FOR ADDITION
APPARATUS AND METHOD FOR ADDITION OF ADH ENZYME INHIBITORS TO EXISTING ENGINE COOLING SYSTEMS

CROSS-REFERENCE TO RELATED APPLICATIONS

This application claims the benefit of priority to U.S. Provisional Patent Application No. 62/391,997 filed May 16, 2016, the contents of which are fully incorporated by reference.

FIELD

The present invention relates to both apparatus and methods for the addition of alcohol dehydrogenase (ADH) enzyme inhibitors to existing engine cooling systems to reduce or eliminate the coolant toxicity without the need to completely drain and replace the entire engine coolant. In addition, the present invention provides an apparatus and method for ADH enzyme inhibitor treatment of otherwise toxic coolants removed from engine cooling systems that are targeted for disposal and release into the environment and thereby eliminates the condition of creating relatively large amounts of toxic waste during routine cooling system maintenance and repairs.

BACKGROUND

The following discussion to set the background for the present discussion can be found in U.S. Pat. No. 8,206,607, entitled Reduced Toxcity Ethylene Glycol-Based Antifreeze/Heat Transfer Fluid Concentrates And Antifreeze/Heat Transfer Fluid Concentrates And Antifreeze/Heat Transfer Fluids. As noted therein, for many years, antifreeze/heat transfer fluid concentrates have been used to form aqueous solutions used to cool internal combustion engines. These concentrates have also been used for deicing solutions used, for example, to device airplanes or power lines. Diols, polyhydric alcohols having two hydroxyl groups such as, for example, alkylene glycols, are often used as the base material for these antifreeze/heat transfer fluid concentrates. Diols typically make up 95% by weight of the antifreeze/heat transfer fluid concentrate and, after blending with water, about 40% to 60% by volume of the solution used for cooling the engine in a vehicle. Conventional antifreeze/heat transfer fluid concentrates have for years been formulated using ethylene glycol (EG) as the base material. EG has proved to be an efficient and cost effective means of providing freezing and boiling protection for engine coolants. In addition to its use in engine coolants, EG is used in a variety of other applications, including production of polyethylene terephthalate for use in polyester films, fibers, and resins.

EG has a number of properties that make it particularly suitable as an antifreeze in automobile engine coolants. When EG is added to water, the freezing point of the mixture is reduced to a safe level for cold weather. For example, a mixture of 50% water and 50% EG has a freezing point of 35.6° below zero Celsius (96° below zero Fahrenheit). In addition, EG has a very low vapor pressure compared to water. As a result, when a mixture of EG and water is heated, as in an internal combustion engine, the EG evaporates from the mixture at a rate very much less than the water. Accordingly, the mixture continues to have sufficient EG to prevent freezing in cold temperatures. Because of the relatively low vapor pressure of EG, mixtures of EG and water can retain their antifreeze characteristics for an extended period of time, while mixtures of water and more volatile alcohols cannot. The extended life of EG/water mixtures is particularly desirable in automobile engine coolants.

Another property of EG that is useful in an antifreeze is its specific gravity. EG has a specific gravity that is significantly greater than the specific gravity of water, and mixtures of EG and water have a higher specific gravity than pure water. For example, at 37.8° C. (100° F.), a mixture of 50% EG and 50% water has a specific gravity that is 6.2 percent greater than water at the same temperature. The concentration of EG in a mixture of EG and water can be easily determined by measuring the specific gravity of the mixture with a hydrometer, an inexpensive and easy to use device. Because the specific gravity is directly related to the concentration of EG in the solution, and the concentration of EG is in turn directly related to the freezing point of the solution, the specific gravity measurement can be used to determine easily whether there is sufficient EG in the solution.

While EG has served effectively as a freeze point depressant and boiling point elevator for engine coolants, its major disadvantage is its toxicity to humans and other mammals if ingested. In the late 1960's and early 1970's, toxicity and environmental concerns resulted in the elimination of chromate and arsenite additives from engine antifreezes and coolants. Since that time, however, formulations have changed little. Our continuing attention to environmental problems has caused renewed concern about the health effects and disposal problems associated with engine EG antifreezes/heat transfer fluid concentrates.

Reports and studies made by The American Association of Poison Control Center's National Data Collection System stated that there were over 1.1 million poisonings reported by 63 poison control centers. These 63 centers serve about half of the U.S. population. About 92% of the reported poisonings occurred in the home and the majority were accidental (89%). Children under six years of age were involved in 62% of the incidences and ingestion accounted for 77% of the poisoning exposures. This same report noted 2451 poisonings related to glycols with 2372 exposures being accidental and, of those, 765 were related to children under six years of age.

In considering toxicity and disposal issues associated with antifreeze/heat transfer fluid concentrates, it is helpful to break down an engine antifreeze/coolant into its component parts (similar parts are found in all EG and water-based thermal fluids):

(1) Water—the primary heat removal fluid. The water content of a solution used as an engine coolant is typically 40% to 70% by volume depending upon the severity of the winter climate. In some warm weather areas, freezing temperatures are not encountered, and water with a corrosion prevention additive is used, or EG (with additives) is added solely to raise the boiling point of the coolant solution.

(2) Freezing Point Depressant and Boiling Point Elevator—in most cases EG is used in a range of 30% to 60% by volume to prevent freezing of the water during the winter. Addition of EG also raises the boiling point of the solution, and the same range of EG is typically used during the summer in temperate regions and year round in warmer climates.

(3) Additive Package—typically contains several different chemicals that are initially added to the glycol to form an antifreeze or concentrate and eventually blended with water to form the coolant. These additives are designed to prevent corrosion, deposit formation, and foaming, and are typically each present in concentrations of 0.1% to 3% by weight of the coolant concentrate.

(4) Contaminants—build up as the engine is used, and result from the following: thermal or oxidative breakdown of glycol lube oil and fuel accumulation metals from cooling system corrosion.

$LD_{50}$ values (acute oral toxicity test ratings) are useful in comparing the relative toxicities of substances. The $LD_{50}$ value for a substance is the dose level (in mg/kg of body weight) administered at the beginning of a two-week period required to kill 50 percent of a group of laboratory rats. A coolant material that has an $LD_{50}$ value of 5,000 mg/kg or lower may be classified as hazardous, with lower $LD_{50}$ ratings indicative of increased toxicity. EG has an acute oral toxicity ($LD_{50}$) of 4,700 mg/kg. Although marginally hazardous by this rating system, EG is a known toxin to humans at relatively low levels (reported as low as 1,570 mg/kg in Toxic Release Inventory Reporting, Notice of Receipt of Petition, Federal Register, Vol. 63, No. 27, Feb. 10, 1998) and consequently is classified by many regulatory authorities as a hazardous material. In addition, EG has a sweet smell and taste, making it attractive to children and animals.

The toxicity associated with EG is caused by the metabolites of EG, some of which are toxic. EG, when ingested, is metabolized to glycoaldehyde by alcohol dehydrogenase (ADH), an enzyme necessary for the conversion. Glycoaldehyde further metabolizes to glycolic acid (glycolate). The accumulation of glycolic acid causes metabolic acidosis. Also, glycolic acid accumulation correlates with a decrease in arterial bicarbonate concentration. Some of the glycolic acid metabolizes to glyoxylic acid (glyoxylate), which further metabolizes to oxalic acid (oxylate). Oxalic acid binds to serum calcium in the bloodstream, and precipitates as crystals of calcium oxalate.

Characteristic symptoms observed with EG ingestion include anion gap metabolic acidosis, hypocalcemia, cardiac failure, and acute oliguric renal failure. Calcium oxylate crystals in many cases can be found throughout the body. Calcium oxylate crystals in the kidneys cause or are associated with the development of acute renal failure.

There are known to be two basic treatments for EG poisoning, both interfering with action of the ADH enzyme to prevent the first metabolism in the chain of events, namely, the metabolism of EG into glycoaldehyde. Until recently, ethanol had been the standard antidote for EG poisoning. There is one FDA-approved antidote: fomepizole (4-methylpyrazole), which is trademarked Antizol and was approved by the FDA in 1997. As reported by Jacobsen in "New treatment for ethylene glycol poisoning", New Eng. J. of Med., Vol. 340, No. 11, Mar. 18, 1999, the series of required fomepizole treatments costs approximately $4,000. Due to the relatively high cost of fomepizole treatment, ethanol is still often used to treat EG poisoning.

Ethanol is the substrate for the ADH enzyme, which means that the ADH enzyme has a great affinity for ethanol to the exclusion of other substances. If enough ethanol is present, the ingested EG gets "crowded out" by the ethanol and is prevented from becoming metabolized. Ethanol, rather than EG, gets metabolized and the metabolites of ethanol are generally less harmful. While the ethanol is being metabolized, the unmetabolized EG has time to pass through the body and be expelled in wastes.

The amount of ethanol required to treat EG poisoning is considerable. As reported by Stipetic and Hobbs, "Tex Tox: Shaken, Not Stirred", Central Texas Poison Center, Jan. 8, 1999, for maximum efficacy, the desired serum ethanol concentration should be maintained between 100-150 mg/dL. This concentration should be maintained until levels of EG are undetectable and the metabolic acidosis has been corrected. Patients that are treated with ethanol (treatment that may last several days) become intoxicated and are at risk for developing hypoglycemia. Additionally, patients must be monitored for elevated liver enzymes.

Fomepizole is a far more effective treatment for EG poisoning than is ethanol because it blocks the action of the ADH enzyme so as to prevent the conversion of EG into glycoaldehyde. Far less fomepizole is required for treatment than ethanol. For example, a fomepizole treatment regime may consist of administering a loading dose of 15 mg/kg, followed by doses of 10 mg/kg every 12 hours for 4 doses, then 15 mg/kg every 12 hours thereafter until EG levels have been reduced below 20 mg/dL. A victim of EG poisoning, whether treated with ethanol or fomepizole, also requires treatment with sodium bicarbonate to counteract ongoing production of organic acids and hemodialysis to remove the glycolic acid that may have been produced by metabolism of EG between the time of ingestion and the start of treatment.

Ethanol is not a practical ADH enzyme inhibitor for use in heat transfer fluid concentrates because it is relatively ineffective for this purpose. Also, ethanol, with a boiling point of 169° F. (76° C.) is too volatile for a coolant ingredient. Additionally, its flash point of 65° F. (18.3° C.) is unacceptable. Fomepizole lacks practicality as an ADH enzyme inhibitor for use in an antifreeze/heat transfer fluid concentrate because of its great expense. Thus, the two heretofore known substances for the treatment of EG poisoning are poor candidates for use as preventatives of poisoning in mixtures with EG.

Worldwide nearly 400 million gallons of antifreeze/heat transfer fluid concentrates are sold every year and incorporated into engine cooling systems. It is estimated that a significant percentage of such engine cooling systems are disposed of improperly, resulting in contamination of the environment. Improper disposal by consumers is a major cause of this environmental contamination. Another major source of environmental contamination is leakage, spills and overflows from heavy duty vehicles. Experience with heavy duty vehicles shows that it is common to lose 10% of the antifreeze/heat transfer fluid volume after every 12,000 to 18,000 miles of operation due to leaks in the system components, such as the water pump, hose or clamps or radiator core. This rate of loss is equal to about one gallon/month for the typical highway truck, which is the equivalent of a leakage rate of one drop per minute. An antifreeze/heat transfer fluid leak rate of one drop per minute is likely to go unnoticed, but can in total add up to a significant loss.

In some operations using heavy duty vehicles, overflows account for far more antifreeze/heat transfer fluid loss than low level leaks at the water pump, hose clamps or radiator core. Overflows occur due to overheating or when a cooling system is overfilled. When a cooling system is overfilled, operation of the engine heats the antifreeze/heat transfer fluid, causing expansion of the fluid that cannot be contained in the system. Pressure relief valve lines typically allow excess fluid to escape to the ground. Small EG spills and leaks (less than a gallon) of antifreeze/heat transfer fluid eventually will biodegrade with little impact to the environment. However, before biodegradation occurs, these spills and leaks can present a toxic danger to pets and wildlife.

The use of EG mixed with water in an engine coolant solution can also result in release of concentrated EG into the environment. At 200° F. (93.3° C.), the vapor pressure of water is 600 mm Hg, while the vapor pressure of EG at that temperature is just 10 mm Hg. Antifreeze/heat transfer fluid solutions used in internal combustion engines will typically start as 50% antifreeze (95% of the antifreeze being EG) and 50% water. Due to the difference in vapor pressure between water and EG, the solution will tend to become more concentrated in EG as water evaporates through "breathing" of the cooling system. Also as a result of the vapor pressure difference, heated antifreeze/heat transfer fluid solution that has been expelled from a cooling system will readily concentrate toward straight EG in the environment, increasing its oral toxicity. The hotter the solution expelled from the cooling system, the more rapidly the water content will pass into the atmosphere, leaving the more concentrated EG behind. Even though temporarily reduced in its hazardous rating level when diluted with water, EG and water-based antifreeze/heat transfer fluid solutions will approach EG's concentrated $LD_{50}$ value of 4,700 mg/kg when the solution is passed out of an automobile's cooling system vent into the environment. When the water is removed from the coolant solution, the antifreeze/heat transfer fluid concentrate is essentially returned to its initial concentrated state, and it is released into the environment as a hazardous, poisonous substance.

Accordingly, a need remains for a convenient apparatus and method to provide consumers the ability to partially remove a relatively small portion of vehicle coolant from an engine coolant system, and to detoxify via an ADH enzyme inhibitor such removed portion for safer environment disposal, so that the remaining coolant in the system can then be treated and detoxified. By also adding a relatively small amount of an ADH enzyme inhibitor, the remaining coolant is also placed in a condition where it can still efficiently provide engine cooling performance, and to the extent that such remaining coolant is partially replaced with the ADH enzyme inhibitor added, its environmental leaking, venting and/or disposal problems will be reduced or completely attenuated.

SUMMARY

A method for treating a water based engine cooling system containing ethylene glycol comprising determining the amount of ethylene glycol (EG) present in the engine cooling system and determining the amount of engine coolant initially present within the engine cooling system to be partially removed for replacement with a selected amount of an alcohol dehydrogenase (ADH) enzyme inhibitor. This is followed by removing the determined amount of coolant and replacing with the selected amount of ADH enzyme inhibitor.

The present invention also relates to a method for treating a water based engine cooling system containing ethylene glycol that comprises determining the amount of ethylene glycol (EG) present in the engine coolant and introducing into the engine cooling system a selected amount of ADH enzyme inhibitor to achieve the following:

$$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is to be introduced into the engine cooling system and the weight of EG is the weight of EG in the engine coolant.

The present invention also relates to a kit for the treatment of a water based engine cooling system containing ethylene glycol (EG) comprising a first container including a selected amount of ADH enzyme inhibitor for treatment of a selected amount of engine coolant containing ethylene glycol to be removed from an engine cooling system and and a second container including a selected amount of ADH enzyme inhibitor for introduction into the engine cooling system. The selected amount of ADH enzyme inhibitor for introduction into the engine cooling system achieves the following:

$$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is to be introduced into the engine cooling system and the weight of EG is the weight of EG in the engine coolant.

The present invention also relates to a kit for the treatment of a water based engine cooling system containing ethylene glycol (EG) comprising a container including ADH enzyme inhibitor for treatment of engine coolant present in the engine cooling system and instructions for a consumer to determine the amount of ADH enzyme inhibitor to add to the engine coolant system so that the engine cooling system achieves the following:

$$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is to be introduced into the engine cooling system and the weight of EG is the weight of EG in the engine coolant.

DETAILED DESCRIPTION

The present invention stands directed at apparatus and methods for the addition of selected amounts of alcohol dehydrogenase (ADH) enzyme inhibitors to existing engine cooling systems to reduce or eliminate coolant toxicity as well as the use of such inhibitors for treatment and safe disposal of toxic coolants removed from engines. Reference to alcohol dehydrogenase (ADH) enzyme inhibitors means any substance that, when mixed with EG and ingested, prevents or substantially diminishes the production of the various toxic metabolites that are related to EG poisoning. Such ADH enzyme inhibitor may therefore preferably include polyhydric alcohols (alcohols that have two hydroxyl or —OH groups) that combine and form blended mixtures with the EG. Reference to blend mixtures with EG should be understood as a mixture wherein the ADH enzyme inhibitor and EG will not phase separate. Preferred ADH enzyme inhibitors herein include propylene glycol (PG)

and/or glycerol. In addition, such ADH enzyme inhibitors are also preferably those that have a boiling point above 150° C. (320° F.).

For a given and existing engine cooling system, the amount of ADH enzyme inhibitor that is preferably introduced may vary. The goal, however, is to transform an existing aqueous based EG based engine cooling system, which is toxic, into an ADH enzyme inhibitor/EG blend, such that the EG remaining in the coolant is rendered non-toxic, and the ADH enzyme inhibitor/EG blend can still provide requisite cooling to the engine as needed. Accordingly, it is preferred that the percent of ADH enzyme inhibitor that is developed in the engine cooling system is one where as shown in Equation 1 below, the value of:

$$\frac{\text{Weight of ADH Enzyme Inhibitor}}{\text{Weight of EG Within the Engine Coolant}}$$

is preferably in the range of 1.0 percent by weight and 30.0 percent by weight. More preferably, the value is in the range of 1.0 percent to 15.0 percent, or even more preferably, in the range of 1.0 percent to 10.0 percent or 1.0 percent to 5.0 percent or 1.0 percent to 2.5 percent. Preferably, the treated engine coolant is such that the mixture of EG/ADH enzyme inhibitor (e.g. PG) is one that is less toxic than 10,000 mg/kg on an acute $LD_{50}$ (rat) oral toxicity basis.

Stated another way, the following (Equation 2) is preferably established upon addition of the ADH enzyme inhibitor to an existing engine cooling system:

$$\frac{\text{Weight of ADH Enzyme Inhibitor}}{\text{Weight of EG Within the Engine Coolant}} = 0.01 \text{ to } 0.30$$

wherein the weight of ADH enzyme inhibitor is the amount of ADH enzyme inhibitor that is to be introduced into the engine cooling system and the weight of EG is the weight of EG in the engine coolant (the weight of EG in the total engine coolant in the engine).

Figure 1:
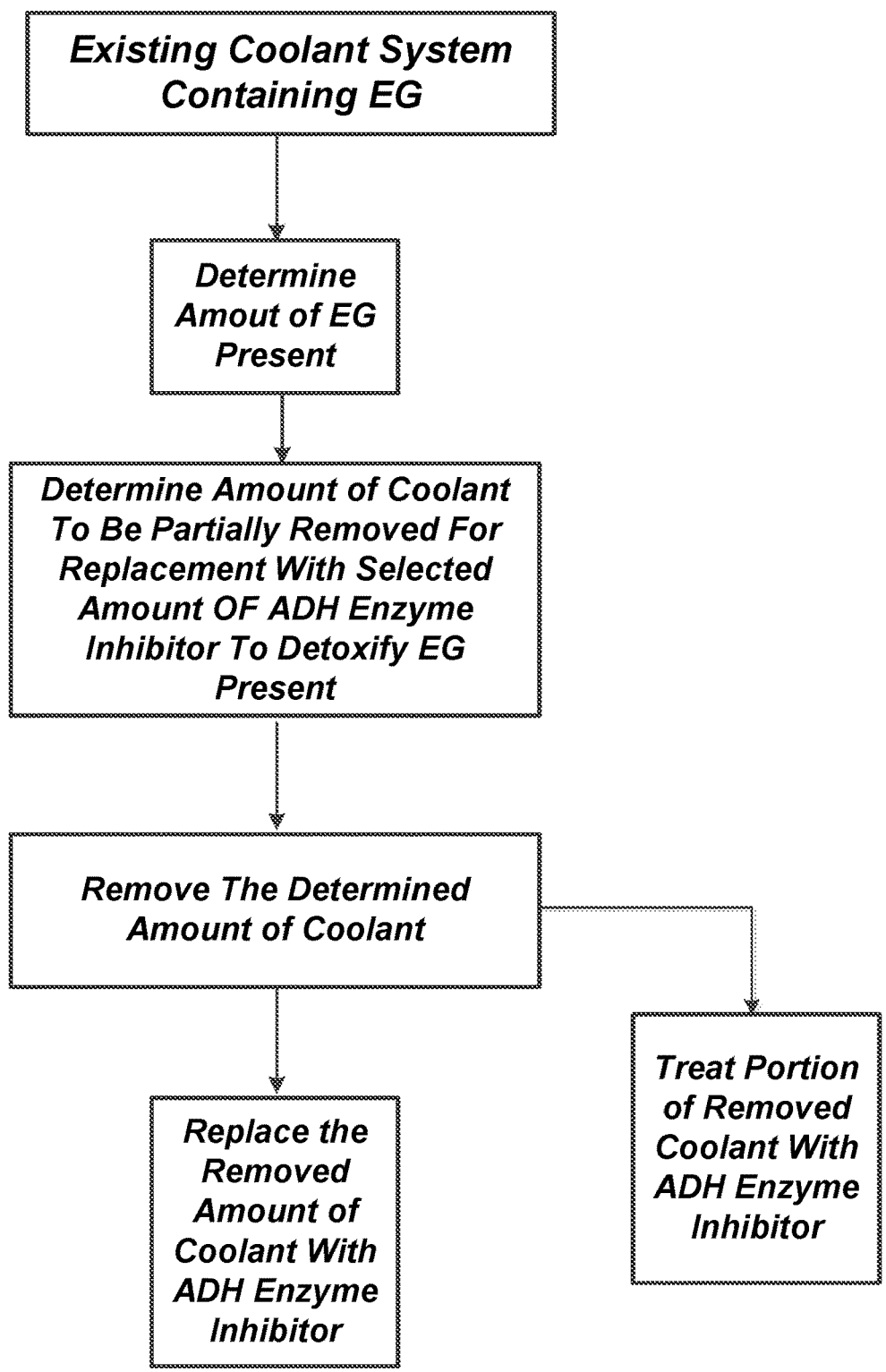
FIG. 1 illustrates a flow-chart outlining one method of the present invention.

Attention is next directed to FIG. 1. In accordance with a method of the present invention, for a given coolant system that contains EG, one determines the relative amount of EG in the aqueous based coolant that is present in the system that requires detoxification. For example, one considers whether or not the coolant system that contains EG is a 50% EG 50% water system, 60% EG/40% water system or 70% EG/30% water system. Then, one can determine the amount of such coolant that can be partially removed which is then removed and the EG portion is replaced by the selected amount of ADH enzyme inhibitor so that detoxification can be achieved. In addition, for the coolant that is removed and placed in the disposal section of the kit, such is also now treated with an appropriate amount of ADH enzyme inhibitor so that it may be disposed of in an environmentally sound manner. Preferably, the coolant that is removed is also immediately treated so that the toxicity of the EG glycol component is less toxic than 10,000 mg/kg on an acute $LD_{50}$ (rat) oral toxicity basis.

Figure 2:
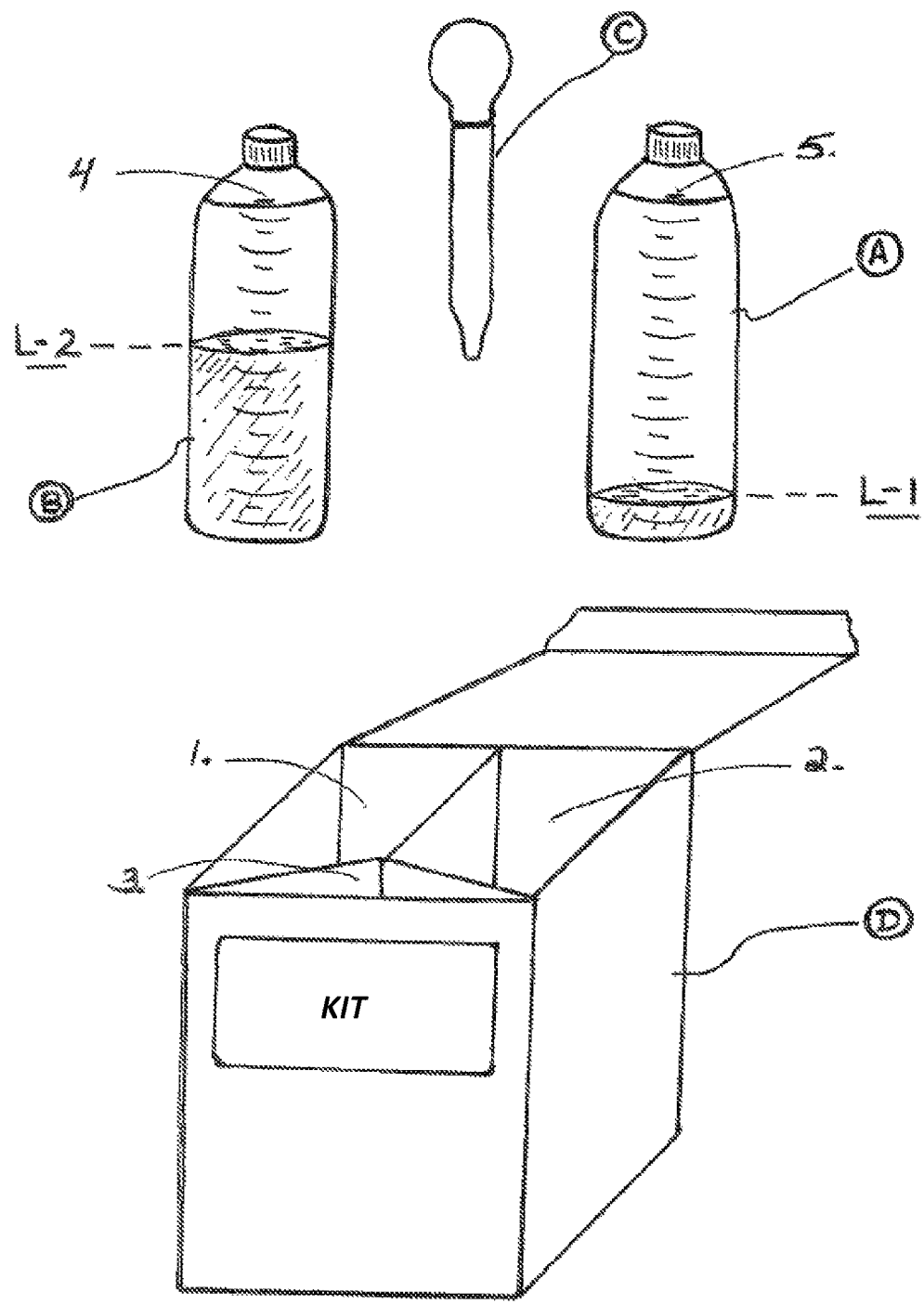
FIG. 2 illustrates one preferred configuration of a kit for use by a consumer for treatment of an engine cooling system.

The above method may preferably be achieved by a kit that can now be supplied to the consumer. Attention is directed to FIG. 2. As can be seen, the kit can be supplied to the consumer in packaging D that preferably contains compartments 1, 2 and 3. The three compartments can contain bottle A which is a graduated container (marked with volume levels) that includes a selected amount of ADH enzyme inhibitor shown generally at L-1 to accommodate and treat a selected amount of waste coolant that is removed from the engine cooling system. Bottle B is another graduated container from which a selected amount of ADH enzyme inhibitor is drawn for introduction into the engine cooling system, if a selected amount of engine coolant is removed to accommodate the introduction of the ADH enzyme inhibitor. Also shown as item C is a squeeze bulb to extract the desired amount of coolant from the engine to be placed in graduated container A for treatment with a selected amount of ADH enzyme inhibitor for safe disposal. Such kit may therefore be preloaded with requisite levels of ADH enzyme inhibitor in graduated containers A and B to detoxify a selected engine cooling system of up to a particular size and having up to a particular volume of coolant. In addition, the kit can optionally include a device to determine the relative concentration of EG in the existing engine cooling system that is to be treated, so that if necessary, the consumer is alerted to the need to utilize additional amounts of ADH enzyme inhibitor if the engine coolant to be treated has some unusually high level of EG present (e.g., levels of EG in the EG/water coolant that exceeds 50% by weight).

In addition, it is worth noting that if the consumer determines that the level of EG present in their particular EG/water cooling system is actually less than 50% by weight, the preloaded quantities of ADH enzyme inhibitor that are present in graduated cylinders A and B may only partially be utilized or left as supplied and need not be adjusted, as having an excess of ADH enzyme inhibitor, both in treatment of the engine (cylinder B) and treatment of the coolant that is removed (cylinder A) is not a disadvantage and can actually serve to provide a "buffer" to maintaining the detoxified condition of the the engine coolant at issue, in the event that the EG levels are inadvertently increased by the consumer.

It can therefore be appreciated that the kit apparatus of FIG. 2, combined with the methods of the present invention, reduces or eliminates problems associated with previous approaches for installation of ADH enzyme inhibitors to detoxify an engine's EG cooling system. The problems of difficulty of use, complexity in determining the actual treatment levels for the engine coolant and the removed coolant are now eliminated by the kit apparatus of FIG. 1. In addition, it is worth nothing that the entire engine coolant does not have to be removed, and as discussed further herein, with respect to the step of needing to remove a determined amount of coolant, it is now only necessary to remove less than or equal to 20.0%, at the most, of the volume of engine coolant that is initially present. More preferably, one need only remove less than or equal to 15.0% of the volume of engine coolant present, or less than or equal to 10.0% of engine coolant volume present, or less than or equal to 5.0% of the volume of engine coolant that is present, or less than or equal to 1.25% of the volume of engine coolant that is present.

A more detailed description of the kit apparatus of FIG. 1 would, by way of example for a typical 2.0 gallon system, proceed as follows. First, one would remove the cap on the expansion tank of a given engine coolant system. Using the squeeze bulb C one can remove sufficient coolant from the expansion tank and/or radiator to transfer and fill the waste coolant bottle A to top mark 5. As can be seen, waste coolant bottle A may be supplied at L-1 with about 0.5 oz (14.8 cc) of the ADH enzyme inhibitor (PG). The 0.5 oz of AHD enzyme inhibitor (PG) will then mix with any EG/water coolant that is removed and render the EG fraction non-toxic. That is, the EG/water coolant that is removed from the engine is treated with a sufficient amount of ADH enzyme inhibitor such that it is less toxic than 10,000 mg/kg on an acute $LD_{50}$ (rat) oral toxicity basis.

Next, the treatment mixing bottle B is selected which is typically a 14.0 oz capacity bottle and is set in total volume to be used in this example for up to a 2.0 gallon EG/water cooling system. The bottle B is supplied with about 214 cc of the ADH enzyme inhibitor (PG) which is shown at L-2 and is the desired amount of treatment of PG fluid. This is based on PG toxicity testing results described herein to treat the system with preferably about 5.0% PG by weight relative to the weight of EG present (see again Equation 1). Bottle B is then filled with water to the fluid mark 4. At that point the ADH enzyme inhibitor/water mixture in bottle B is ready for addition to the engine. Below is the relevant calculation for such treatment:

Two gallon engine coolant system made up of a 50/50 EG/water blend contains 1 gallon of EG for treatment
1 gallon of EG equals 128 oz which equals 3,785 cc.
Density of EG is 1.115 g/cc
3785 cc×1.115 g/cc=4220.2 g of EG present
Goal is to provide 5.0% PG relative to the EG present
Using Equation 1, the amount of PG to achieve at least 5.0% PG of the total weight of glycol present indicates the need to provide 211 g of PG.
PG density is 1.036 g/cc
211 g (PG)×1 cc/1.036 g=203.6 cc of PG into bottle B at L-2.

As may be appreciated, if higher concentrations of PG are desired, then the amount of PG in bottle B may be increased. In addition, it can be seen that for a two gallon engine coolant system, containing 50% EG/water, a relatively small amount of the engine coolant can be removed (about 410 cc) so that about 203.6 cc of PG and 203.6 cc of water can be introduced to provide for a non-toxic engine coolant system. It can be appreciated that upon removal of 410 cc of, in this example, the two gallon 50/50 EG water blend, such would remove 205 cc of EG, thereby removing about 228.6 g of EG. Accordingly, when introducing 211 g of PG, the percent of ADH enzyme inhibitor (PG) relative to the ethylene glycol component present is as follows: 211 g PG/3992 g EG=0.053.

It is next worth noting that the present invention need not rely upon what is illustrated in FIG. 2. That is, in certain engine cooling systems, it may not be necessary to first remove any particular amount of the EG/water coolant as there will be adequate space in the engine coolant expansion tank or even within a given radiator tank, and the requisite amount of ADH enzyme inhibitor that may be necessary to detoxify the EG present may be introduced directly into such an engine cooling system with no removal of any coolant. For the convenience of consumers in connection with such engine cooling systems, one may supply graduated containers of ADH enzyme inhibitor that is calculated, according to Equation 1, to provide an amount of ADH enzyme inhibitor where the percentage of ADH enzyme inhibitor (e.g. PG) relative to the total weight of glycol component present again falls in the range of 1.0 percent to 30.0 percent.

As alluded to above, the preferred amount of ADH enzyme inhibitor that is introduced into a given engine coolant system will result in improved $LD_{50}$ such that the glycol component is less toxic than 10,000 mg/kg on an acute $LD_{50}$ (rat) oral toxicity test basis. It can now be appreciated that the toxicity levels that can be achieved herein when utilizing ADH enzyme inhibitor have been tested and determined to be as follows:

| | |
|---|---|
| 5.0% PG/95.0% EG | 15,000 mg/kg $LD_{50}$ |
| 10.0% PG/90.0% EG | 24,000 mg/kg $LD_{50}$ |
| 30.0% PG/70.0% EG | >40,000 mg/kg $LD_{50}$ |

Moreover, optionally, within the kits described herein, one may include and introduce into the engine coolant, along with the ADH enzyme inhibitor discussed herein, various other additives to impart desired characteristics to the coolant. Such additives may include buffers, corrosion inhibitors, dyes, scale inhibitors, surfactants or chelants.

It can now be appreciated that the present invention provides an apparatus and method to allow consumers to treat existing cooling systems containing EG via removal of only a relatively small portion of the engine coolant (e.g., less than or equal to 20% of the volume of coolant present) followed by treatment with a selected amount of ADH enzyme inhibitor. Engine coolants may be those present in automobiles, trucks, agricultural equipment (e.g. tractors) and commercial engines (e.g. industrial compressors or rock/metal crushing machines), or any internal combustion engine that relies on liquid cooling systems. In addition, to the extent that any coolant is removed to accommodate the addition of ADH enzyme inhibitor, such removed coolant is also rendered non-toxic. Consumers now may convert a previously toxic engine coolant to a non-toxic engine coolant, while maintaining the original cooling capacity of the system.

Finally, after the addition of the ADH enzyme inhibitor as described herein, the engine's coolant system will be non-toxic in the event of a system leakage such as what may be typically realized in an overheat condition. Furthermore, the coolant herein will be rendered non-toxic for any future drainage required for coolant system repair or routine periodic coolant changes, maintain a much more safer environment.

The invention claimed is:

1. A method for treating an existing water based engine cooling system containing ethylene glycol comprising:
   determining the amount of ethylene glycol (EG) present in said engine cooling system;
   determining the amount of engine coolant initially present within the engine cooling system to be partially removed for replacement with a selected amount of an alcohol dehydrogenase (ADH) enzyme inhibitor; and
   removing said determined amount of coolant and replacing with said selected amount of ADH enzyme inhibitor.

2. The method of claim 1 wherein said engine coolant, after replacement with said selected amount of ADH enzyme inhibitor, is less toxic than 10,000 mg/kg on an acute $LD_{50}$ (rat) oral toxicity test basis.

3. The method of claim 1 wherein said ADH enzyme inhibitor comprises propylene glycol.

4. The method of claim 1 wherein said amount of engine coolant to be partially removed for replacement with a selected amount of alcohol dehydrogenase (ADH) inhibitor comprises less than or equal to 20.0% of the volume of engine coolant initially present.

5. The method of claim 1 wherein said selected amount of alcohol dehydrogenase (ADH) enzyme inhibitor that is introduced into said engine to replace the determined amount of coolant provides as follows:

$$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is introduced into the engine coolant system and the weight of EG is the weight of EG in the engine coolant.

6. The method of claim 1 wherein the replacing with said amount of ADH enzyme inhibitor includes the addition of at least one of a buffer, corrosion inhibitor, dye, scale inhibitor, surfactant or chelant.

7. The method of claim 1 wherein said engine cooling system is an engine cooling system of an internal combustion engine.

8. The method of claim 1 wherein said internal combustion engine is in an automobile, truck, agricultural or commercial engine.

9. A method for treating a water based engine cooling system containing ethylene glycol comprising:
   determining the amount of ethylene glycol (EG) present in said engine cooling system; and
   introducing into said engine cooling system a selected amount of ADH enzyme inhibitor to achieve the following:

$$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is introduced into the engine cooling system and the weight of EG is the weight of EG in the engine coolant.

10. A kit for the treatment of a water based engine cooling system containing ethylene glycol (EG) comprising:
    a first container including a selected amount of ADH enzyme inhibitor for treatment of a selected amount of engine coolant containing ethylene glycol to be removed from an engine cooling system;
    a second container including a selected amount of ADH enzyme inhibitor for introduction into the engine cooling system;
    wherein said selected amount of ADH enzyme inhibitor for introduction into the engine cooling system achieves the following:

$$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is introduced into the engine cooling system and the weight of EG is the weight of EG in the engine coolant.

11. A kit for the treatment of a water based engine cooling system containing ethylene glycol (EG) comprising:
    a container including ADH enzyme inhibitor for treatment of engine coolant present in said engine cooling system;
    instructions for a consumer to determine the amount of ADH enzyme inhibitor to add to said engine cooling system so that said engine cooling system achieves the following $$\frac{\text{Weight of } ADH \text{ Enzyme Inhibitor}}{\text{Weight of } EG \text{ Within the Engine Coolant}} = 0.01 \text{ to } 0.30$$

wherein the weight of ADH enzyme inhibitor is the amount of ADH enzyme inhibitor that is introduced into the engine cooling system and the weight of EG is the weight of EG in the engine coolant.

\* \* \* \* \*